(12) United States Patent
Lewis et al.

(10) Patent No.: US 12,004,893 B2
(45) Date of Patent: Jun. 11, 2024

(54) SYSTEMS AND METHODS FOR ARTIFACT DETECTION FOR IMAGES

(71) Applicant: GE Precision Healthcare LLC, Wauwatosa, WI (US)

(72) Inventors: Chelsey A Lewis, Waukesha, WI (US); Michelle DeLong Samalik, Waukesha, WI (US); Brian E Nett, Waukesha, WI (US); Mark Ciesko, Waukesha, WI (US); Jonathan R Polhamus, Waukesha, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 981 days.

(21) Appl. No.: 16/943,897

(22) Filed: Jul. 30, 2020

(65) Prior Publication Data

US 2022/0031273 A1  Feb. 3, 2022

(51) Int. Cl.
*A61B 6/00* (2006.01)
*A61B 6/03* (2006.01)
*A61B 6/46* (2024.01)

(52) U.S. Cl.
CPC .............. *A61B 6/527* (2013.01); *A61B 6/032* (2013.01); *A61B 6/037* (2013.01); *A61B 6/465* (2013.01); *A61B 6/488* (2013.01)

(58) Field of Classification Search
CPC ......... A61B 6/527; A61B 6/032; A61B 6/037; A61B 6/465; A61B 6/488
See application file for complete search history.

(56) References Cited

U.S. PATENT DOCUMENTS

| | | | |
|---|---|---|---|
| 2014/0328450 A1* | 11/2014 | Pal | A61B 6/032 378/20 |
| 2017/0042494 A1* | 2/2017 | Kim | G06T 11/006 |
| 2019/0150857 A1* | 5/2019 | Nye | G16H 30/40 |
| 2019/0231296 A1* | 8/2019 | Jackson | A61B 6/488 |
| 2020/0065940 A1* | 2/2020 | Tang | G06T 3/40 |
| 2020/0160511 A1* | 5/2020 | Lyman | G06T 3/40 |

\* cited by examiner

*Primary Examiner* — Bobbak Safaipour
*Assistant Examiner* — Jongbong Nah

(57) ABSTRACT

Systems and methods for obtaining images are described. A method may include detecting a patient residing on a table proximate the system and detecting one or more artifact areas within an anatomical scan range of the patient. In some examples, the method can include generating an artifact area indicator for the system to display, wherein the artifact area indicator comprises data indicating a location for each of the one or more artifact areas that reside within the anatomical scan range of the patient.

20 Claims, 8 Drawing Sheets

SYSTEMS AND METHODS FOR ARTIFACT DETECTION FOR IMAGES

FIELD

Embodiments of the subject matter disclosed herein relate to non-invasive diagnostic imaging, and more particularly, to detecting artifact areas and providing feedback for patient positioning to avoid known artifact areas in images.

BACKGROUND

Non-invasive imaging technologies allow images of the internal structures of a patient or object to be obtained without performing an invasive procedure on the patient or object. In particular, technologies such as computed tomography (CT), among others, use various physical principles, such as the differential transmission of x-rays through an imaging region of interest or a target volume, to acquire image data and to construct tomographic images (e.g., three-dimensional representations of the interior of the human body or of other imaged structures).

SUMMARY

This summary introduces concepts that are described in more detail in the detailed description. It should not be used to identify essential features of the claimed subject matter, nor to limit the scope of the claimed subject matter.

In an aspect, a system for obtaining images may include a processor that may detect one or more artifact areas within an anatomical scan range and generate an artifact area indicator for the system to display, wherein the artifact area indicator comprises data indicating a location for each of the one or more artifact areas that reside within the anatomical scan range.

In some examples, the system is an x-ray imaging system, a computed tomography (CT) imaging system, a magnetic resonance imaging (MRI) system, a positron emission tomography (PET) imaging system, or a single-photon emission computed tomography (SPECT) imaging system, and combinations thereof. In some examples, the one or more artifact areas may be located on a table, within a table, in an imaging accessory proximate to a table, or a combination thereof. The processor can also detect the one or more artifact areas in a pre-scan configuration of the system without acquiring an image.

In some examples, the processor can capture one or more camera images of a patient residing on a table, detect a location of the patient on the table from the one or more camera images, and detect that the one or more artifact areas are within the anatomical scan range based at least in part on the location of the patient and the one or more artifact areas proximate the table or proximate an imaging accessory coupled to the table. In an aspect, the processor may also detect the one or more artifact areas in an initialization image acquired by the system.

In some examples, the one or more artifact areas represent one or more metallic objects or non-metallic objects in a pre-configured component or an unknown component of the system. In some aspects, the artifact area indicator may be displayed by the system on a display device electronically coupled to the system with a wired interface, a wireless interface, a projected image displayed on the table, or a combination thereof. In some examples, the processor may obtain an initialization image of the patient residing on the table and detect the one or more artifact areas from the initialization image. In some examples, the one or more artifact areas reside within a head holder coupled to the system.

In some examples, the processor may identify the one or more artifact areas based on a predetermined configuration of the one or more artifact areas within a set of components of the system or a detected artifact area indicator affixed to a component of the system. In some examples, the set of components of the system comprise the table, a head holder, a foot extender, a knee support device, or a combination thereof. The processor may also determine an artifact area indicator to provide based on one or more exclusion zones associated with the one or more artifact areas.

In another aspect, a method for obtaining images may include detecting one or more artifacts within a scan range of a patient and generating an artifact area indicator to display, wherein the artifact area indicator comprises data indicating a location for each of the one or more artifact areas that reside within the scan range of the patient. In some examples, the method can include displaying the artifact area indicator using one or more display devices.

In an aspect, a non-transitory, machine-readable medium for obtaining images can include a plurality of instructions that, in response to execution by a processor, cause the processor to detect a patient residing on a table proximate an imaging system. The plurality of instructions can also cause the processor to detect one or more artifact areas within a scan range of the patient. In some examples, the plurality of instructions can cause the processor to generate an artifact area indicator to display, wherein the artifact area indicator comprises data indicating a location for each of the one or more artifact areas that reside within the scan range of the patient. Furthermore, the plurality of instructions can cause the processor to display the artifact area indicator, wherein the artifact area indicator is displayed by a display device.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present techniques will be better understood from reading the following description of non-limiting examples, with reference to the attached drawings, wherein below.

DETAILED DESCRIPTION

Figure 5:
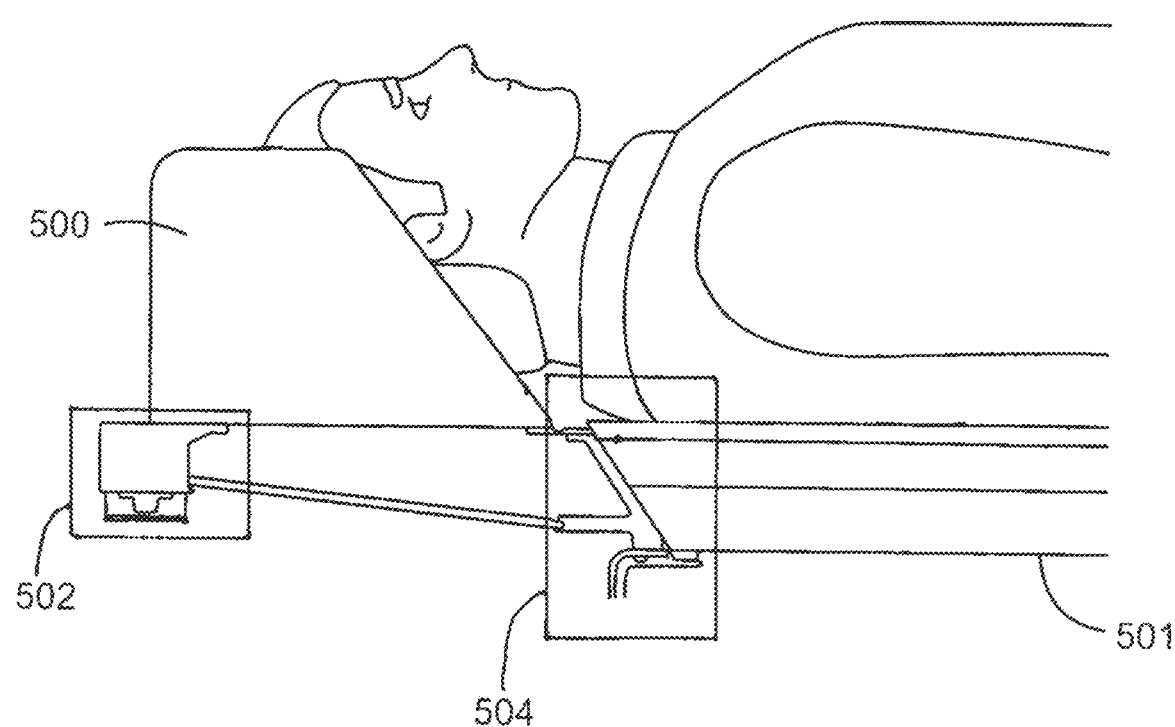
FIG. 5 shows a schematic diagram illustrating an example head holder with artifact areas according to examples described herein.
Figure 6A:
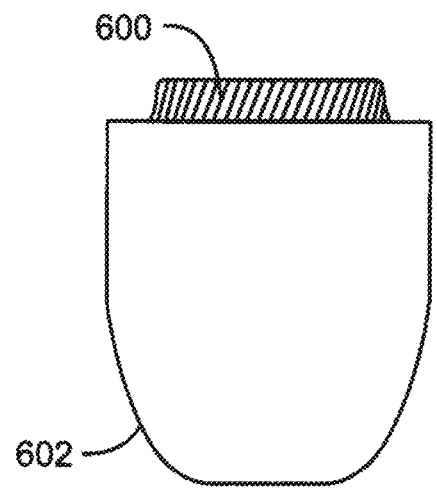
FIGS. 6A and 6B depict an example artifact area indicator affixed to a portion of an example head holder according to examples described herein.
Figure 6B:
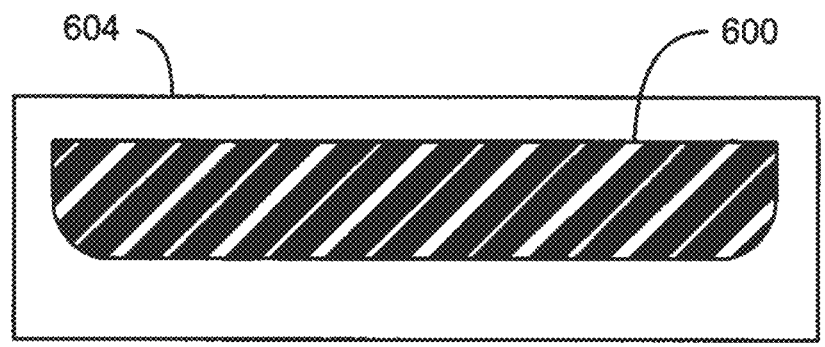
Figure 7:
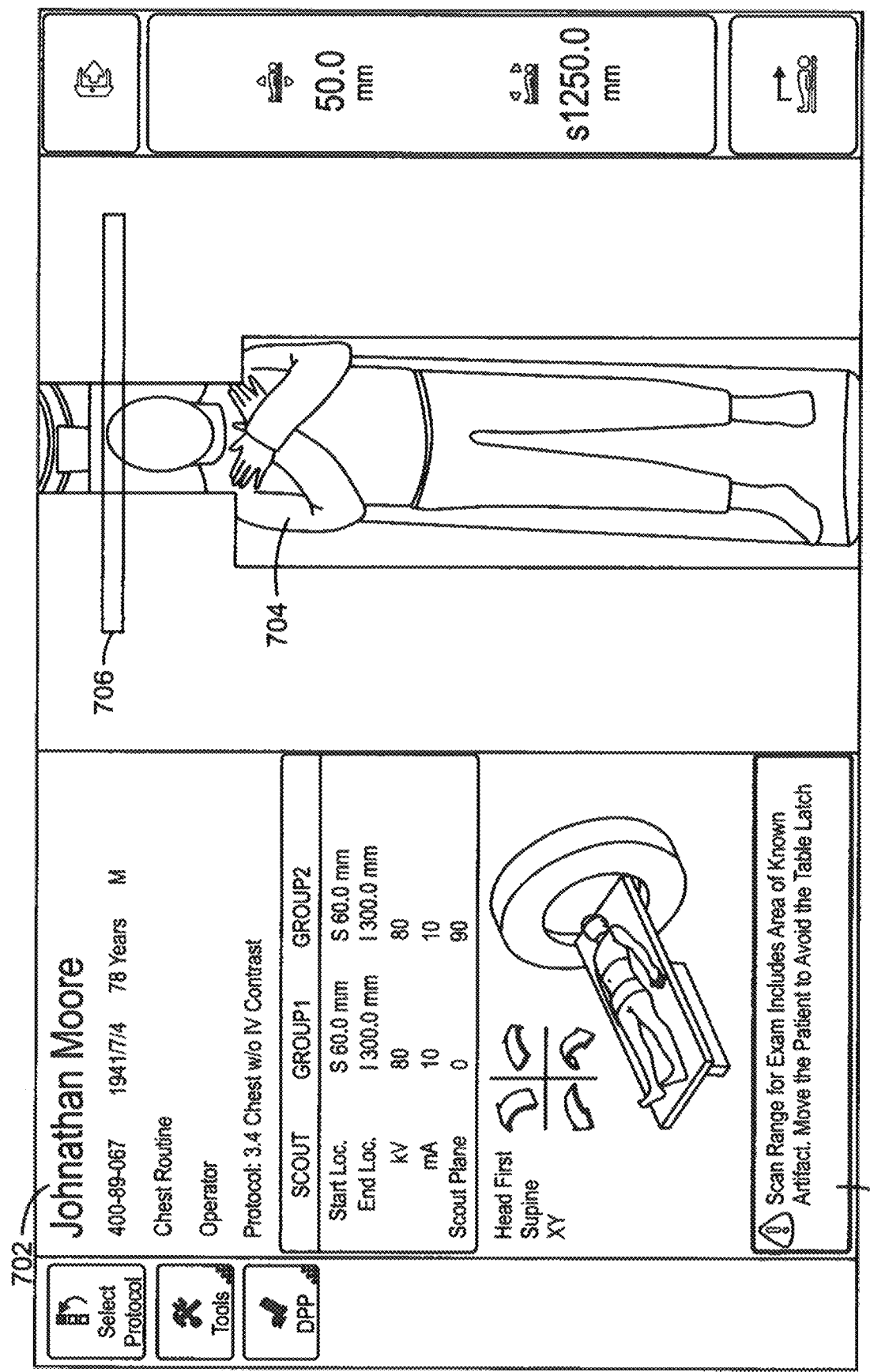
FIG. 7 shows an example screen shot of a user interface generated from a pre-scan acquisition of an imaging system according to examples described herein.
Figure 8:
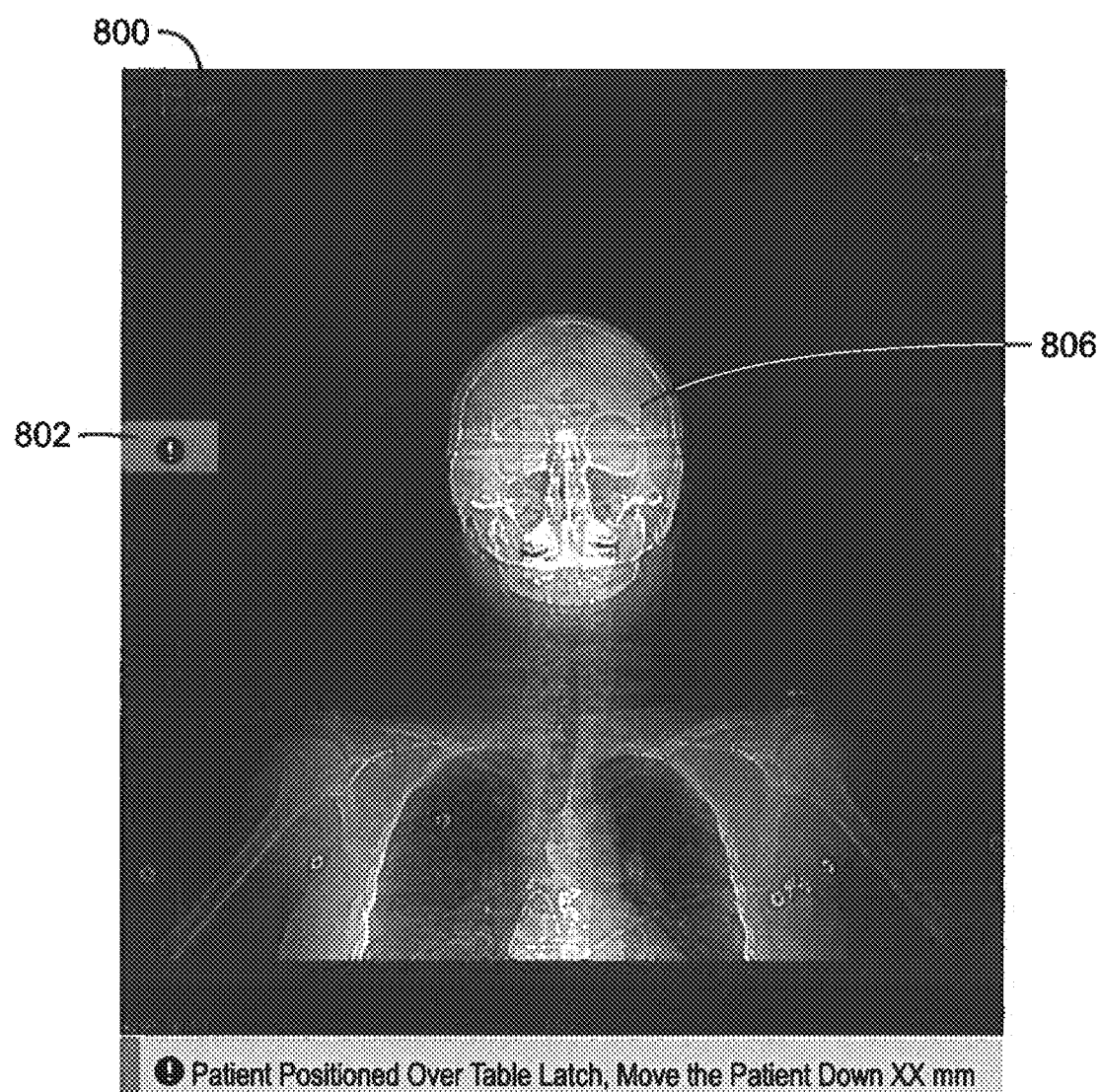
FIG. 8 shows an example image generated from an initialization scan of an imaging system according to examples described herein.
Figure 9:
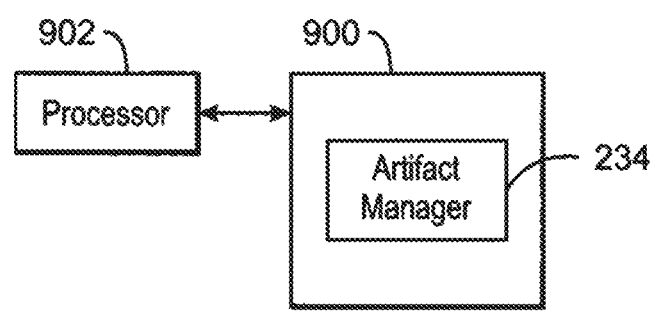
FIG. 9 shows a block diagram of an example non-transitory, machine-readable medium for detecting artifact areas within a scan range according to examples described herein.

Embodiments of the present disclosure will now be described, by way of example, with reference to FIGS. 1-9, in which the following description relates to various examples of imaging systems. In particular, systems and methods are provided for generating images that do not include artifacts. An artifact, as referred to herein, can include any metallic object, non-metallic object, table seam or gap, component, imaging accessory, or the like, that obscures or obfuscates an image. An example of an imaging system that may be used to acquire images processed in accordance with the present techniques is provided in FIGS. 1 and 2. One approach to detecting artifact areas, such as the methods depicted in FIGS. 3 and 4, may include detecting artifact areas within an anatomical scan range of a patient and generating artifact area indicators to be displayed or otherwise provided. FIG. 5 shows an example imaging accessory with potential artifact generating areas. In some examples, artifact area indicators may be affixed to portions of an imaging accessory to indicate potential artifact generating areas as illustrated in FIGS. 6A and 6B. FIGS. 7 and 8 show examples of a pre-scan acquisition and an initialization scan, respectively. FIG. 9 provides a block diagram of an example non-transitory, machine-readable media for detecting artifact areas that could create artifacts in images.

The technical effect of detecting artifact areas in a scan range of an imaging region of interest of a patient can prevent the generation of non-diagnostic areas, or obscured, blurry, or obfuscated areas of an image. Accordingly, the present techniques have a technical advantage of reducing a time period to perform a series of imaging scans of a patient by ensuring that the series of imaging scans do not include artifacts. The present techniques can also reduce the data storage and processing time of an imaging system by determining if potential artifact generating areas reside within a scan range of a patient prior to capturing a series of images. Furthermore, a technical advantage of the present techniques can include reducing the dosage of x-ray radiation that a patient is exposed to by acquiring images in a single imaging scan rather than requesting the acquisition of additional images due to image artifacts in the acquired images.

Though a CT imaging system is described by way of example, it should be understood that the present techniques may also be useful when applied to images acquired using other imaging modalities, such as an x-ray imaging system, a magnetic resonance imaging (MRI) system, a positron emission tomography (PET) imaging system, a single-photon emission computed tomography (SPECT) imaging system, and combinations thereof (e.g., multi-modality imaging systems, such as PET/CT, PET/MR, or SPECT/CT imaging systems). The present discussion of a CT imaging system is provided merely as an example of one suitable imaging system.

Figure 1:
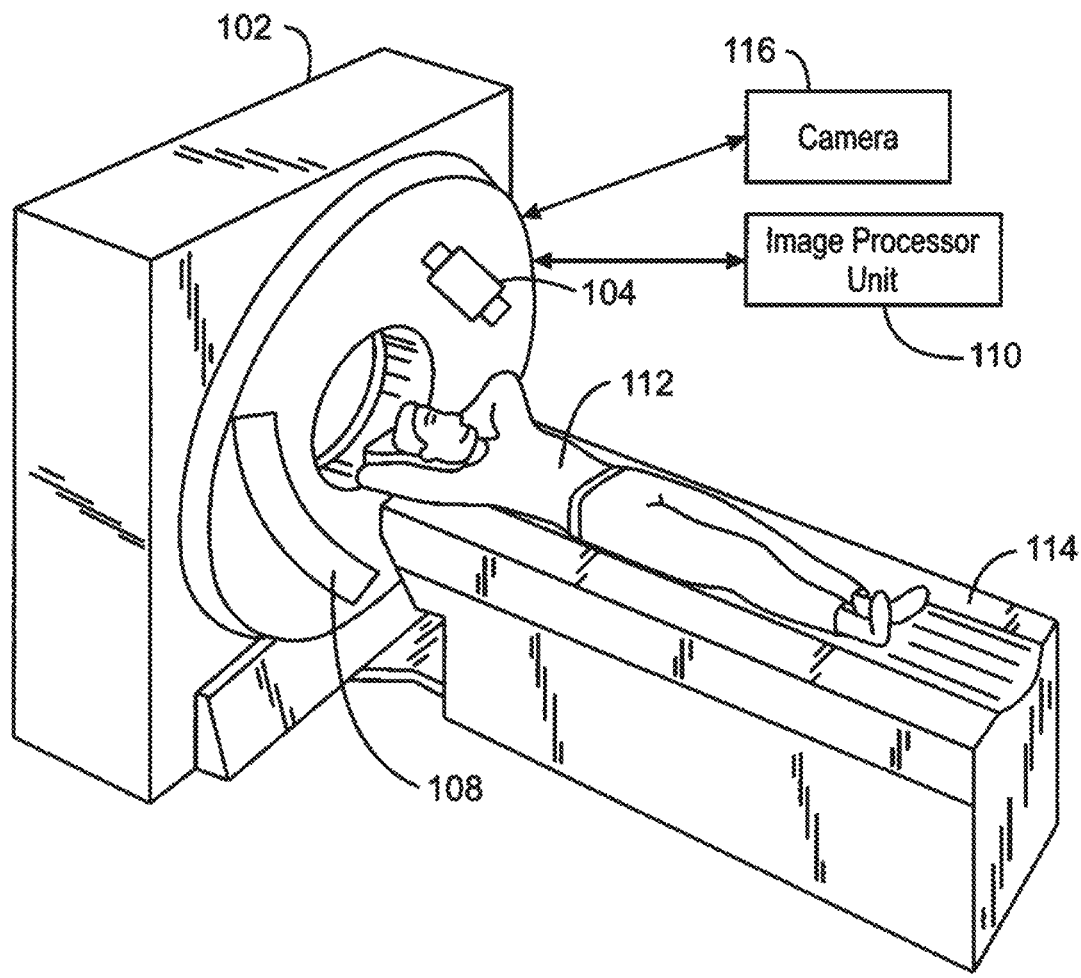
FIG. 1 shows a pictorial view of an example imaging system according to examples described herein.

FIG. 1 illustrates an example imaging CT imaging system 100 configured for CT imaging. Particularly, the CT imaging system 100 is configured to image a subject 112 such as a patient, an inanimate object, one or more manufactured parts, and/or foreign objects such as implants and/or contrast agents present within the body. In one embodiment, the CT imaging system 100 includes a gantry 102, which in turn, may further include at least one x-ray source 104 configured to project a beam of x-ray radiation 106 (see FIG. 2) for use in imaging the subject 112 laying on a table 114. Specifically, the x-ray source 104 is configured to project the x-ray radiation beams 106 towards a detector array 108 positioned on the opposite side of the gantry 102. Although FIG. 1 depicts only a single x-ray source 104, in certain embodiments, multiple x-ray sources and detectors may be employed to project a plurality of x-ray radiation beams 106 for acquiring projection data at different energy levels corresponding to the patient. In some embodiments, the x-ray source 104 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT imaging system 100 further includes an image processor unit 110 configured to identify the subject 112 on the table 114 and determine if artifacts reside within a scan range of the subject 112. For example, the image processor unit 110 can capture camera images of the subject 112, components of the CT imaging system 100, or a combination thereof, from a camera 116 coupled to the CT imaging system 100. The image processor unit 110 can analyze the camera images to determine if artifacts are within a scan range of the subject 112. In some examples, the CT imaging system 100 can also generate artifact indicators to indicate if the subject 112 is to move or be moved to prevent artifacts from appearing in images of the subject 112. The techniques for generating the indicators for artifacts are described in greater detail below in relation to FIGS. 2-9.

In some examples, the image processor unit 110 can determine if artifact areas are present in an imaging region of interest prior to acquiring an initialization image, following the acquisition of the initialization image, or following the acquisition of a diagnostic image or images. For example, the image processor unit 110 can detect potential artifact areas in a region of interest representing a scan range of a subject 112 prior to acquisition of an initialization image, such as a scout image. The initialization image may be any image that uses a low dosage to acquire or capture an initial image for configuring the CT imaging system 102, the placement of the subject 112 on the table 114, and the like. In some examples, the image processor unit 110 may determine if artifact areas are present in a region of interest and provide representations or indicators for the artifact areas following the acquisition of the initialization image. As discussed below in relation to FIGS. 2-9, notifications, representations or indicators of the artifact areas may be displayed on a user interface or added to or merged with the initialization image.

In some examples, initialization images may be acquired between one or more series of imaging scans of a subject 112. For example, the image processor unit 110 may acquire an initialization image following the acquisition of diagnostic images for a protocol or within one or more scan ranges. In some examples, the image processor unit 110 may capture or acquire any number of initialization images in any suitable sequence. The image processor unit 110 may detect and display artifact areas with any number of the initialization images. For example, the image processor unit 110 may acquire consecutive initialization images until an initialization image is acquired without artifact areas within a region of interest or a scan range. In some examples, a single initialization image may be acquired for multiple diagnostic imaging series and the image processor unit 110 may detect artifact areas in any of the region of interest of the multiple diagnostic imaging series. For example, the image processor unit 110 may detect artifact areas within an initialization image acquired from an abdomen, chest, and head, among others, of a subject 112.

In some examples, the image processor unit 110 may acquire one or more initialization images and detect artifacts based on the one or more initialization images. For example, the image processor unit 110 may acquire an anterior posterior (AP) initialization image, a lateral initialization image, or both an AP initialization image and a lateral initialization image, wherein the AP initialization image represents imaging data in a first plane, such as an X-Y plane in the three dimensional cartesian space, and the lateral initialization image represents imaging data in a second plane, such as an X-Z plane or a Y-Z plane in three dimensional cartesian space, among others.

In some examples, the image processor unit 110 may detect artifact areas within a region of interest in a scan range without a camera 116 by acquiring an initialization image and detecting the artifact areas in the initialization image. For example, the image processor unit 110 may implement any suitable machine learning techniques that may identify or detect one or more artifact areas in the initialization image. In some examples, the camera 116 may be used to capture camera images of the subject 112 and provide one or more of the camera images during the pre-acquisition process. In some examples, the image processor unit 110 may detect images of a table without a subject 112 and determine any number of known artifact areas on the table. The artifact areas or regions proximate the artifact areas may be marked or otherwise indicated in a display.

In some examples, the image processor unit 110 may also reconstruct images of a target volume or region of interest of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of a radiation beam by the object. Each detector element of the array produces a separate electrical signal that is a measurement of the x-ray beam attenuation at the detector location. The attenuation measurements from all the detector elements are acquired separately to produce a transmission profile.

In some CT imaging systems, the x-ray source and the detector array are rotated with a gantry within the imaging plane and around the object to be imaged such that an angle at which the radiation beam intersects the object constantly changes. A group of x-ray radiation attenuation measurements, e.g., projection data, from the detector array at one gantry angle is referred to as a "view." A "scan" of the object includes a set of views made at different gantry angles, or view angles, during one revolution of the x-ray source and detector. It is contemplated that the benefits of the methods described herein accrue to imaging modalities other than CT, so as used herein the term "view" is not limited to the use as described above with respect to projection data from one gantry angle. The term "view" is used to mean one data acquisition whenever there are multiple data acquisitions from different angles, whether from a CT imaging system or any other imaging modality including modalities yet to be developed as well as combinations thereof.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

In an "axial" scan, a CT table with the patient positioned thereon may be moved to the desired location and then maintained stationary while the x-ray beam is rotated within the gantry, collecting data. A plurality of measurements from slices of a target volume may be reconstructed to form an image of the entire volume.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude examples of the present techniques in which data representing an image is generated but a viewable image is not. Therefore, as used herein, the term "image" broadly refers to both viewable images and data representing a viewable image. However, many embodiments generate (or are configured to generate) at least one viewable image.

Figure 2:
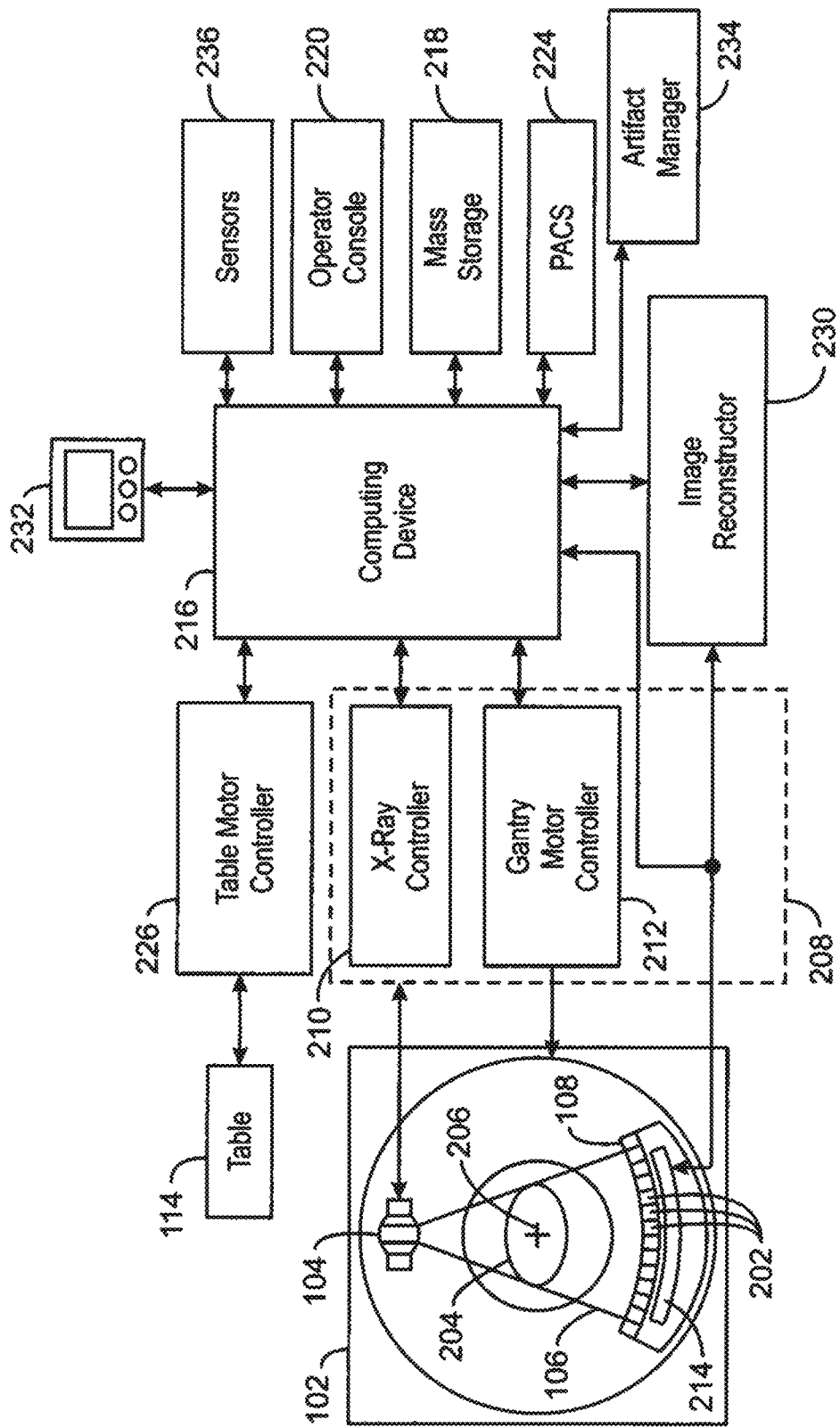
FIG. 2 shows a block schematic diagram of an example imaging system according to examples described herein.

FIG. 2 illustrates an example imaging system 200. In accordance with aspects of the present disclosure, the imaging system 200 is configured for imaging a patient or subject 204 (e.g., the subject 112 of FIG. 1). In one embodiment, the imaging system 200 includes the detector array 108 (see FIG. 1). The detector array 108 further includes a plurality of detector elements 202 that together sense the x-ray radiation beam 106 (see FIG. 2) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an example implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the region of interest of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely and may be operatively connected to the imaging system 200 using a wired or wireless network. In some examples, computing resources in a "cloud" network cluster may be used for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

In some examples, the imaging system 200 may implement an artifact manager 234 for identifying or detecting artifacts and acquiring images. For example, the artifact manager 234 may include a graphical user interface provided to the display device 232 of the imaging system 200. The graphical user interface displayed by the display device 232 may provide a live video stream of a patient on a table 114 of the imaging system 200, an initialization image with detected artifacts, or the like. In some examples, the artifact manager 234 may be stored in the storage device 218. The storage device 218 may also store sensor data from any number of sensors 236 that enables detecting artifacts. The sensors 236 may include, in some examples, a gyroscope, an accelerometer, an ambient light sensor, a camera, and the like. The sensors 236 may receive or capture patient location data that may include camera images, pressure sensor data, or any other sensor data, that indicates a position or location of a patient on the table 114 of the imaging system 200. For example, the sensor data may indicate a location of a region of interest of a subject on a table and the artifact manager 234 may use the sensor data to determine if artifact areas are located in the region of interest. In some examples, the sensors 236 may be electronically coupled to the computing device 216 or the sensors 236 may be coupled to the CT imaging system 102 and the computing device 216 may receive the sensor data from the CT imaging system 102 with any suitable wired or wireless interface. In some examples, the sensors 236 may detect sensor data for a table 114 that may be either vertically positioning or horizontally positioned proximate the imaging system 200.

In some examples, the computing device 216, the CT imaging system 102, or any combination thereof, may execute instructions received or generated by the artifact manager 234. The artifact manager 234 may be stored in the mass storage 218, in memory (not depicted) of the computing device 216, in memory (not depicted) of the CT imaging system 102, or in any suitable storage device or memory device coupled to the CT imaging system 102. In some examples, the artifact manager 234 may generate instructions for providing one or more indicators that represent or indicate artifacts present in a region of interest of a subject 112. For example, the artifact manager 234 may analyze and compare the position of a subject 112 to a target area for a scan. If the patient location information indicates that artifact areas are present in a region of interest of the subject 112, the artifact manager 234, using the computing device 216, the CT imaging system 102, or any combination thereof, may provide any number of artifact indicators to help the subject 112 move or change positions. The artifact indicators may include any number of graphical user interface depictions, warnings, lights, audio messages, projections, and the like. In some examples, the computing device 216 may generate the artifact indicators and transmit instructions to the CT imaging system 102 to provide the artifact indicators to the subject 112.

In some examples, the display 232 coupled to the computing device 216 enables an operator or clinician to access or view data from the artifact manager 234 and to evaluate the imaged anatomy. The display 232 may also allow the operator to select a volume of interest (VOI) and/or request patient information, for example, via a graphical user interface (GUI) for a subsequent scan or processing. In some examples, the display 232 may be electronically coupled to the computing device 216, the CT imaging system 102, or any combination thereof. For example, the display 232 may receive data, such as artifact indicators, from the artifact manager 234, and provide the artifact indicators to a subject 102 or clinician proximate the CT imaging system 102 by displaying the artifact indicators on the display 232. In some examples, the display 232 may display or provide the artifact indicators to clinicians or operators proximate the computing device 216. The computing device 216 may be located proximate the CT imaging system 102 or the computing device 216 may be located in another room, area, or a remote location.

In some examples, the artifact manager 234 may be partially, or entirely, implemented in hardware of the CT imaging system 102, the computing device 216, or any combination thereof. For example, the functionality of the artifact manager 234 may be implemented with an application specific integrated circuit, logic implemented in an embedded controller, or in logic implemented in a processor, among others. In some examples, the functionality of the artifact manager 234 may be implemented with logic, wherein the logic, as referred to herein, includes any suitable hardware (e.g. a processor, a graphics card, or the like), software (e.g. an application, an operating system, or the like), firmware, or any suitable combination of hardware, software, and firmware.

The various methods and processes (such as the methods described below with reference to FIG. 3) described further herein may be stored as executable instructions in non-transitory memory on a computing device (or controller) in imaging system 200. In one embodiment, the table motor controller 226, x-ray controller 210, gantry motor controller 212, image reconstructor 230 and artifact manager 234 may include such executable instructions in non-transitory memory, and may apply the methods described herein to provide artifact indicators. In another embodiment, computing device 216 may include the instructions in non-transitory memory, and may apply the methods described herein, at least in part, to detect artifacts created by components of the imaging system 200. In yet another embodiment, the methods and processes described herein may be distributed across the CT imaging system 102 and the computing device 216.

Figure 3:
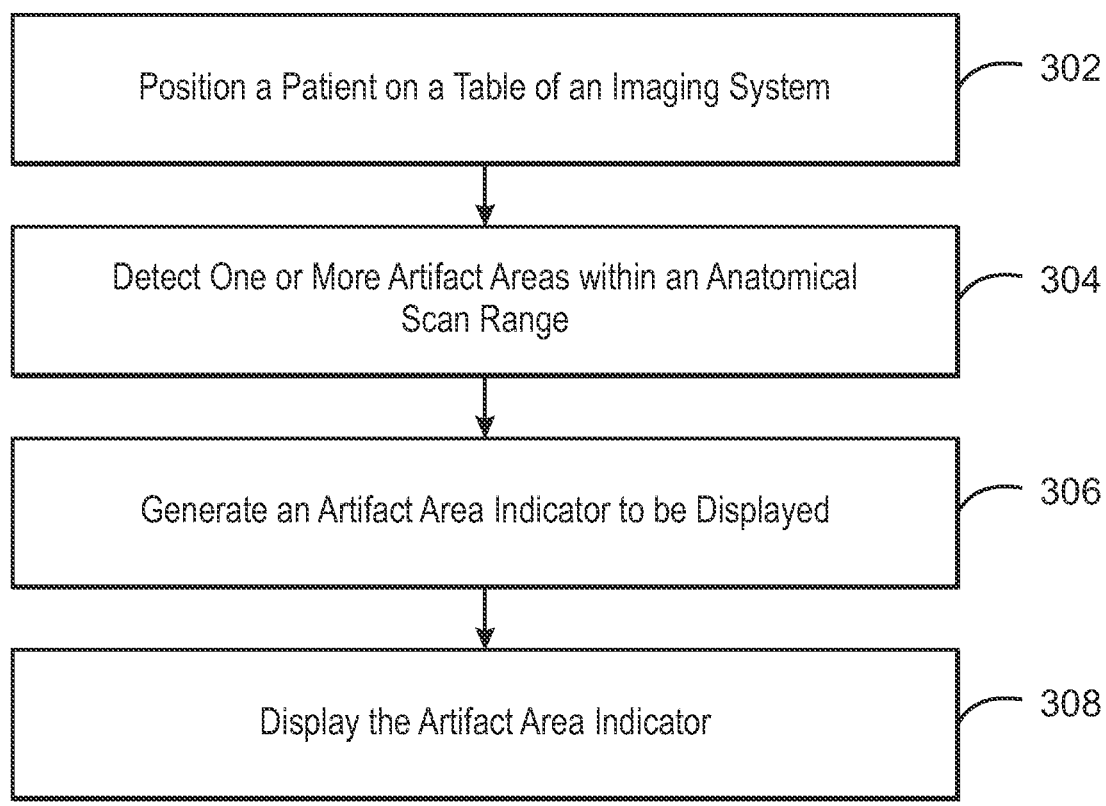
FIG. 3 shows a process flow diagram illustrating an example method for detecting artifact areas within a scan range according to examples described herein.

FIG. 3 illustrates an example process flow diagram for detecting artifact areas within a scan range for a patient. In some examples, the method 300 may be implemented with any suitable device such as the CT imaging system 102 or the imaging system 200 of FIG. 2.

At step 302, the method 300 may include positioning a patient on a table of an imaging system.

At step 304, the method 300 may include detecting one or more artifact areas within a predetermined anatomical scan range of the patient. In some examples, the artifacts correspond to metal components, or components manufactured from other materials, that can obfuscate an image of a patient. For example, the artifact areas can reside within a head holder coupled to a CT imaging system, within foot extenders, and the like. In some embodiments, the method 300 can include identifying the one or more artifact areas based on a predetermined configuration of the one or more artifact areas within a set of components of the system. For example, the predetermined configuration can indicate locations of artifact areas within the components of a CT imaging system. The components of the system can include a table, a head holder, a foot extender, a knee pad support device, electrodes, child positioning equipment, a chin strap, a table pad, a cradle overlay, or any other imaging accessory or any combination thereof. In some examples, any number of the components or imaging accessories may be used in a CT scan of a patient. For example, a head holder and a knee support device may be used in a full body scan image of a patient.

In some examples, the method 300 can include determining a region of interest or target volume of the patient or subject to scan for CT imaging. For example, the method 300 can include determining a region of interest and a scan range for a protocol corresponding to an image or series of images to be acquired. In some examples, the method 300 may also include determining one or more artifact areas within a scan range of the CT image acquisition based on the region of interest or target volume of the patient to scan. For example, the method 300 may include detecting one or more artifact areas that may create an artifact in an image or images. As discussed above, the artifact areas may include metallic objects, non-metallic objects, and the like, that obscure one or more areas of an image or images acquired from the area of interest of a patient.

Still at step 304, in some examples, the method 300 may include detecting the artifact areas within a scan range for a single image or a series of images based on a protocol for the scan, a camera image or video, and the like. For example, the artifact areas may be detected before an initial image, such as a scout image, is acquired. In some examples, a live video feed of a patient's position on a table can provide visual feedback indicating whether a patient has shifted to a position that enables a full scan range devoid of artifact areas. In some examples, the artifact areas may be detected from a scout image that displays potential artifact areas in the image.

In some examples, an exclusion zone corresponding to each artifact area may be detected and displayed. The exclusion zone, as referred to herein, may indicate a two-dimensional or a three-dimensional area proximate the detected artifact areas that is to be excluded or located outside of the region of interest. In some examples, a size of the exclusion zone for an artifact area, such as a hinge of a head holder, among others, can be modified. In some examples, each exclusion zone may also be displayed with a different color to indicate different artifact areas. For example, a first artifact area, such as a head holder, among others, may be displayed with a first color and a second artifact area, such as a foot extender, among others, may be displayed with a second color. The size of each exclusion zone may also be different based on the detected artifact areas. For example, a hinge may have an exclusion zone of a first size and an attachment component between a head holder and a table may have an exclusion zone of a second size.

At step 306, the method 300 may include generating an artifact area indicator to be displayed by the system. In some examples, the artifact area indicator indicates or represents whether the patient is aligned on the table without artifact areas in a region of interest for the CT image. For example, the artifact area indicator may indicate if the patient is aligned on the table with at least one artifact area in the scan range of the patient. In some examples, the method 300 may include providing an artifact area indicator representing a detected artifact area to one or more displays electronically coupled to the system. For example, the displays may provide images of scan regions of a patient on a table along with any detected artifact areas from the components or image accessories of the system within the scan range.

In some examples, the method 300 may include determining a type of artifact area indicator to provide based on one or more exclusion zones associated with the one or more artifact areas. For example, the type of artifact area indicator may include a color of an artifact area indicator to provide using a display device, a color of a light to project onto a table, or the like. In some examples, the color of the artifact area indicator represents different exclusion zones or different sizes of exclusion zones. For example, an exclusion zone representing a hinge in a head holder attached to a table of an imaging system may be represented by a first color, a first image, or a first alert, among others, provided to a clinician or patient. In some examples, an exclusion zone representing a metal connector between the head holder and the table may be represented by a second color, a second image, or a second alert, among others.

At step 308, the method 300 may include providing or displaying an artifact area indicator using the imaging system. For example, the method 300 may include projecting information representing the artifact area indicator onto a table proximate the imaging system, displaying the artifact area indicator using a display device coupled to the imaging system, or using a remote display device to display the artifact area indicator. In some examples, artifact area indicators, exclusion zones, or a combination thereof, may be provided within a display device along with an initialization image or scout image, among other information. The exclusion zones may be provided in initialization or scout images that include artifacts or within initialization or scout images that do not contain artifacts. In some examples, the artifact area indicator is provided to the patient so that the patient may move or be repositioned on the table to prevent artifacts from appearing within an image or images. For example, the artifact area indicator may be displayed by a display device proximate the imaging system to enable the patient to view a direction, a distance, or a combination of a direction and a distance to move on the table. In some examples, the patient can be notified to move a predetermined distance based on a live video stream of the patient combined with artifact areas detected on an initialization image. In some examples, the artifact area indicator may be provided to the patient or clinician in a pre-acquisition process prior to acquiring the initialization image or the artifact area indicator may be provided to the patient or clinician within an initialization image, accompanying an initialization image, or as a set of instructions generated based on artifact areas detected within the initialization image.

The process flow diagram of method 300 of FIG. 3 is not intended to indicate that all of the operations of steps 302-308 of the method 300 are to be included in every example. Additionally, the process flow diagram of method 300 of FIG. 3 describes a possible order of executing operations. However, it is to be understood that the operations of the method 300 may be implemented in various orders or sequences. In addition, in some examples, the method 300 can also include fewer or additional operations. For example, the method 300 may include modifying a series of images to be acquired for a protocol based on the detected artifact areas. For example, a scan range may be adjusted or modified to a smaller scan range, a larger scan range, or a scan range with a different starting location, a different ending location, or a combination thereof.

In some examples, the method 300 may include capturing one or more camera images of the patient residing on the table, detecting a location of the patient on the table from the one or more camera images, and detecting that the one or more artifact areas are within the anatomical scan range based at least in part on the location of the patient and a predetermined configuration of the one or more artifact areas proximate the table or proximate a component attached to the table. For example, the predetermined configuration of a head holder may indicate an artifact area is located at a base of the head holder and the camera images may indicate that a scan range of a subject is located above the base of the head holder. In some examples, the method 300 can include generating an artifact area indicator to represent the artifact area at the base of the head holder.

Figure 4:
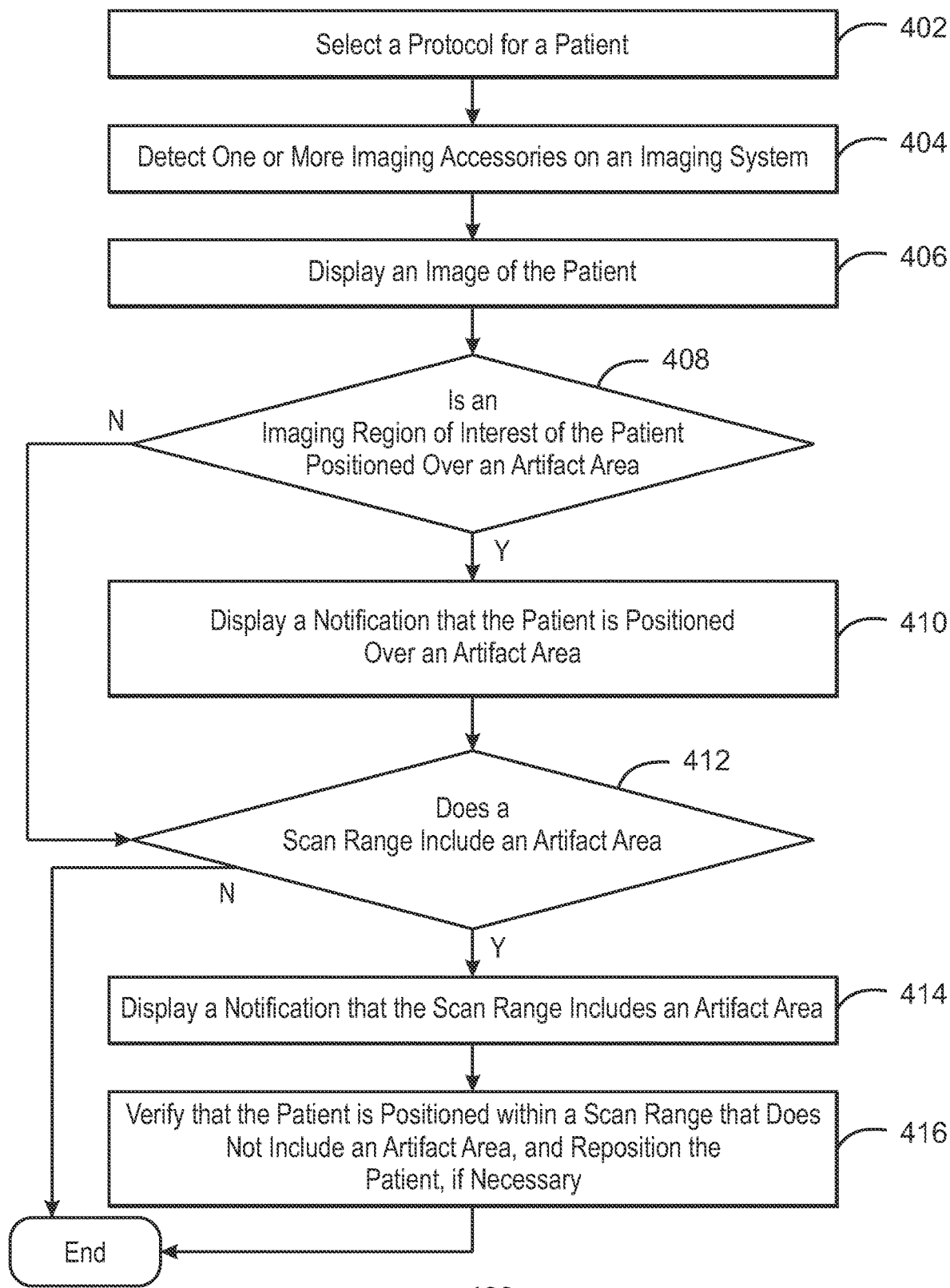
FIG. 4 shows a process flow diagram illustrating an example method for detecting artifact areas within a scan range according to examples described herein.

FIG. 4 illustrates an example process flow diagram of a method for detecting artifact areas. In some examples, the method 400 may be implemented with any suitable device such as the CT imaging system 102 of FIG. 1 or the computing device 216 of FIG. 2, among others.

At step 402, the method 400 includes receiving suggestions for a protocol or otherwise selecting a protocol for a patient. The protocol, as referred to herein, is an imaging technique with a plurality of imaging parameters used to acquire an image or a series of images for a particular region of interest of a subject or patient. In some examples, the protocol may indicate a scan range, a region of interest of the body corresponding to the scan range, a dosage amount, x-ray source settings, and a plurality or other settings or parameters and the like.

The scan range may indicate a starting location and an end location for each image to be acquired by an imaging system. In some examples, a protocol may be shared between multiple patients or each patient may have an individualized protocol. For example, an individualized protocol may specify a scan range based on a height of a patient or a weight of a patient.

At step 404, the method 400 includes detecting or identifying one or more imaging accessories or components coupled to the imaging system. For example, a camera electronically coupled to a CT imaging system may capture images of the CT imaging system and use any suitable technique, such as machine learning techniques, among others, to identify imaging accessories or components coupled to the CT imaging system. The imaging accessories or components may include various types of head holders, foot extenders, knee pad holders, and the like. In some examples, the CT imaging system may receive the images from the camera via any suitable interface such as a wired interface or a wireless interface, among others.

At step 406, the method 400 includes displaying or otherwise providing a video stream of a detected patient residing on a table of the imaging system. For example, the method 400 may include receiving one or more images of the table of the CT imaging system and using a machine learning technique, among others, to identify objects or components placed on the table. In some examples, the method 400 may include determining that an object placed on the table is a patient.

At step 408, the method 400 includes determining whether an imaging region of interest of a patient is positioned over an artifact area.

If the imaging region of interest of the patient is positioned over an artifact area, then the process continues at step 410. At step 410, the method 400 may include displaying or otherwise providing a notification via one or more display devices coupled to the imaging system. The notification may indicate that the patient is positioned over an artifact area. In some examples, the notification may include a display, image, or live stream video of a patient indicating the patient may be positioned over an artifact area and instructions for moving the patient to avoid the artifact area, and the like. If the imaging region of interest of the patient is not positioned over an artifact area, then the process continues at step 412.

At step 412, the method 400 may include determining if the scan range is prescribed within a region of the table or imaging accessories or components coupled to the table that include artifact areas. The artifact areas may include any suitable metal object, such as a hinge, or a connector, among others. In some examples, the artifact areas may include any object manufactured from a material that can obfuscate an image of the patient acquired by the CT imaging system. The artifact areas may be located on the table, within the table, in a component proximate to the table, or a combination thereof. In some examples, artifacts represent one or more metallic objects or non-metallic objects in a pre-configured component or an unknown component of the system. For example, known or pre-configured components may have artifact areas that have known locations. A head holder or a foot extender may have any number of known locations of hinges and connectors. In some examples, unknown components may have artifact areas with unknown locations. The method 400 may include acquiring an initialization image of unknown components to determine the locations of the artifact areas. In some examples, the artifact areas of the unknown artifact areas may be stored in any suitable data repository. If the scan range includes at least one artifact area, the process flow continues at step 414.

At step 414, the method 400 includes displaying an artifact area indicator with information indicating that an artifact area is located within the scan range of a patient. In some examples, the artifact area indicator may also include a display, image, or live video stream of the patient along with exclusion areas corresponding to artifact areas within the scan range. In some examples, the artifact area indicator may be displayed by a display device coupled to a remote computing device, displayed by a display device coupled to an imaging system, such as the CT imaging system, or the artifact area indicator may be projected onto a table within a scan range of a region of interest of a patient or subject. The process flow continues at step 416.

At step 416, the method 400 includes verifying or confirming that a patient is positioned within the scan range that does not include an artifact area. For example, the patient or subject may move or be moved following a notification of artifact areas within a scan range of a region of interest of the patient or subject. In some examples, moving the patient or subject may prevent the need for an initialization image or scout image. The position of the patient may be confirmed or verified by any suitable camera capturing images or video of the patient and using machine learning techniques to detect that the patient has changed positions to prevent artifacts from being created in an image or series of images. The process ends upon completion of step 416. In some examples, at step 412, the process flow can also end if there are not any artifact areas identified within the scan range.

The process flow diagram of method 400 of FIG. 4 is not intended to indicate that all of the operations of steps 402-416 of the method 400 are to be included in every example. Additionally, the process flow diagram of method 400 of FIG. 4 describes a possible order of executing operations. However, it is to be understood that the operations of the method 400 can be implemented in various orders or sequences. In addition, in some examples, the method 400 may also include fewer or additional operations.

FIG. 5 illustrates an example head holder component attached to a table with artifact areas. In some examples, any number of imaging accessories or components, such as a head holder 500, among others, may be attached or coupled to a table 501. The imaging accessories or components may include any number of artifact areas or metallic objects that obscure or obfuscate images. For example, the head holder 500 includes artifact areas 502 and 504 at the base of the head holder 500 and the top of the head holder 500, respectively. In some examples, imaging accessories or components, such as the head holder 500, may include artifact areas at any suitable location such as the base of the head holder 500, the sides of the head holder 500, the middle region of the head holder 500, or the like. In some examples, the artifact areas 502 and 504 may include hinges or connectors, among others, that are constructed of a material that obfuscates images, such as x-ray images, CT images, and the like.

FIGS. 6A and 6B depict an example artifact area indicator affixed to a portion of a head holder. In some examples, the artifact area indicator 600 may be any suitable material, such as an adhesive material, among others, that represents an artifact area in an imaging accessory or component of an imaging system. As illustrated in FIG. 6A, in some examples, the artifact area indicator 600 can be a sticker or material attached to a portion of the head holder, foot extender, knee rest, or the like. The artifact indicator 600 may indicate that the patient is positioned on top of an artifact area and that the patient should be moved to reduce the increased probability of image artifacts in the scan area. In some examples, the artifact area indicator 600 may be placed or affixed to the head holder 602, or any other suitable imaging accessory or component of an imaging system. The artifact area indicator 600 may be placed on the end of a table 604 where the adjustment block is located, at the top of a head holder 602, or proximate any other suitable artifacts area in imaging accessories or components of an imaging system.

In some examples, the artifact area indicator 600 may be placed at any suitable distance from a top of the head holder 602 or within a predetermined distance from an artifact area. For example, the artifact area indicator 600 may be placed within 1 inch, 2 inches, 4 inches, or any other suitable distance from an artifact area. In some examples, the predetermined distance to place the artifact area indicator 600 represents an exclusion zone in which a region of interest of a patient is not to be placed when capturing or acquiring images.

FIG. 6B is a perspective view of an example artifact area indicator 600. The artifact area indicator 600 may be placed around the artifact area or proximate to the artifact area. For example, the artifact area indicator 600 is attached to an extension 604 of a head holder 602. In some examples, any number of artifact area indicators 600 may be attached or affixed to imaging accessories or components of an imaging system. For example, an artifact area indicator 600 may be attached to an extension 604 of a head holder 602, among others.

FIG. 7 is an illustration of an example screen shot of a user interface generated from a pre-scan acquisition for an imaging system. In some examples, the pre-scan user interface 700 may include patient information, protocol information, and any suitable number of images, videos, or a combination thereof. For example, the patient information 702 can include a height of the patient, a weight of the patient, an age, and notes such as locations of implants in the patient, among others. In some examples, the pre-scan user interface 700 may include an image or live video stream 704 of a patient on a table of the imaging system. The pre-scan user interface 700 may also include locations of artifact areas 706, or exclusion zones representing the artifact areas 706. For example, the pre-scan user interface 700 may include a highlighted area indicating the exclusion zone proximate an artifact area within the image or live video stream 704. In some examples, the pre-scan user interface 700 of a patient may include the image or live video stream 704 of the patient on the table with exclusion zones or artifact areas 706 in a merged format that enables a clinician or patient to see a position of the patient in relation to the artifact areas 706. The pre-scan user interface 700 may also include an artifact area indicator 708 that specifies information about the artifact area, a location of the artifact area, and recommended actions to prevent the artifact areas from appearing in an image of a patient. In some examples, the pre-scan user interface 700 may enable detection of the one or more artifact areas in a pre-scan configuration of the system without acquiring an image of the patient.

It is to be understood that the pre-scan user interface 700 may include fewer or additional elements. For example, the pre-scan user interface 700 may include the image or live video stream 704 but may not include patient information 702. The pre-scan user interface 700 may also include additional information related to the patient or subject, the clinician, the imaging system, and the facility for acquiring the images, among others.

FIG. 8 is an illustration of an example initialization image captured by an imaging system. In some examples, the initialization image 800 (also referred to herein as a scout image) may include a single image of a subject or patient. The initialization image 800 may be acquired prior to acquiring the images of a protocol at a higher dosage. The initialization image 800 may include a lower dose of x-ray radiation, among others, and may be used to determine a patient's location or position prior to acquiring a series of images for a protocol such as a head scan, an abdomen scan, or the like. In some examples, the initialization image 800 may include an artifact area indicator 804 or warning in response to an artifact 806 being captured within the initialization image 800. For example, the artifact area indicator 804 may suggest moving a subject or patient a particular distance, a particular direction, or a combination thereof, away from an artifact area 802 to prevent the artifact 806 from obfuscating the image captured during a scan.

In some examples, the artifact area indicator 804 or warning of an artifact area 802 may be included in an initialization image 800 proximate the artifact 806. For example, the artifact area warning 802 may appear proximate any suitable artifact 806 such as a hinge in a head holder, proximate a hinge in a foot extender, or the like. It is to be understood that the initialization image 800 can include fewer or additional elements. For example, the initialization image 800 may include any number of artifact indicators representing or corresponding to any number of artifacts 806 in an initialization image 800. In some examples, the initialization image 800 may also include additional patient information, imaging information, and the like.

FIG. 9 is an example of a non-transitory machine-readable medium for detecting artifact areas within a region of interest or scan range of a subject, in accordance with examples. The non-transitory, machine-readable medium 900 can implement the functionalities of the image processor unit 110 of FIG. 1, the computing device 216 of FIG. 2, or a combination thereof, among others. For example, a processor 902 in a control system of a CT imaging system 102, a computing device 216, or any other suitable device, can access the non-transitory, machine-readable media 900.

In some examples, the non-transitory, machine-readable medium 900 may include instructions to execute an artifact manager 234. For example, the non-transitory, machine-readable medium 900 may include instructions for the artifact manager 234 that cause the processor 902 to generate and provide artifact indicators representing artifacts within a region of interest or scan range of a subject. The non-transitory, machine-readable medium 900 may also include instructions to implement any combination of the features of the artifact manager 234 described in examples above.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. A method for detecting a known artifact area relative to a patient position, the method comprising:
    identifying, via a camera or other sensor, an accessory attached to a table of an imaging system, wherein at least one portion of the accessory is a known artifact area;
    defining, using a computing device of the imaging system, an anatomical scan range of a patient based on a scan protocol;
    detecting, using the computing device of the imaging system, a location of the anatomical scan range of the patient relative to the known artifact area;
    determining, using the computing device of the imaging system, if the known artifact area is positioned within the anatomical scan range of the patient; and
    notifying a user, via a display of the imaging system, that the known artifact area is positioned within the anatomical scan range of the patient.

2. The method of claim 1, further including capturing a camera image of the imaging system to identify the accessory is attached to the table of the imaging system.

3. The method of claim 2, further comprising identifying that the accessory attached to the table is one or more of a head holder, a foot extender, and a pad.

4. The method of claim 3, wherein determining if the known artifact area is positioned within the anatomical scan range of the patient is based on a identifying the accessory attached to the table, wherein each accessory includes a different at least one known artifact area.

5. The method of claim 1, further including capturing a camera image of the patient to determine the location of the anatomical scan range of the patient relative to the known artifact area.

6. The method of claim 1, wherein notifying the user that the known artifact area is positioned within the anatomical scan range of the patient includes providing a suggestion to the user to move the patient out of the known artifact area.

7. The method of claim 6, further comprising, after providing the suggestion to the user, verifying the known artifact area is not positioned within an adjusted location of the anatomical scan range of the patient.

8. A system for detecting a known artifact area relative to a patient position in a medical imaging system, the system comprising:
    a table coupled to the medical imaging system to support a patient, wherein an accessory with a known artifact area is coupled to the table;
    a camera coupled to the medical imaging system to detect the accessory coupled to the table; and
    a display device coupled to the medical imaging system to display to a user that the known artifact area is positioned within a scan range of the patient.

9. The system of claim 8, wherein the medical imaging system is an x-ray imaging system, a computed tomography (CT) imaging system, a magnetic resonance imaging (MRI) system, a positron emission tomography (PET) imaging system, or a single-photon emission computed tomography (SPECT) imaging system.

10. The system of claim 8, wherein the camera detects the accessory is coupled to the table, wherein the known artifact area includes at least one portion of the accessory.

11. The system of claim 8, wherein the camera identifies a location of the scan range of the patient relative to the known artifact area of the accessory coupled to the table.

12. The system of claim 8, wherein the accessory includes one or more of a head holder, a foot extender, and a pad.

13. The system of claim 8, further including a sensor to detect a location of the scan range of the patient relative to the known artifact area of the accessory coupled to the table.

14. The system of claim 13, wherein the sensor includes one or more of a gyroscope, an accelerometer, a pressure sensor, and an ambient light sensor.

15. A method for detecting a known artifact area relative to a patient position, the method comprising:
    identifying, via a camera or other sensor, an accessory attached to a table of an imaging system, wherein at least one portion of the accessory is a known artifact area;
    defining, using a computing device of the imaging system, an anatomical scan range of a patient based on a scan protocol;
    acquiring an initial image of the patient using the imaging system;
    detecting, using the computing device of the imaging system, a location of the anatomical scan range of the patient relative to the known artifact area;
    determining, using the computing device of the imaging system, if the known artifact area is positioned within the anatomical scan range of the patient; and
    notifying a user, via a display of the imaging system, that the known artifact area is positioned within the anatomical scan range of the patient.

16. The method of claim 15, further including capturing a camera image of the imaging system to identify the accessory is attached to the table of the imaging system.

17. The method of claim 16, further comprising identifying that the accessory attached to the table is one or more of a head holder, a foot extender, and a pad.

18. The method of claim 17, wherein determining if the known artifact area is positioned within the anatomical scan range of the patient is based on a identifying the accessory attached to the table, wherein each accessory includes a different at least one known artifact area.

19. The method of claim 15, wherein notifying the user that the known artifact area is positioned within the anatomical scan range of the patient includes providing a suggestion to the user to move the patient out of the known artifact area.

20. The method of claim 19, further comprising, after providing the suggestion to the user, verifying the known artifact area is not positioned within an adjusted location of the anatomical scan range of the patient.

* * * * *